(12) United States Patent
Portal et al.

(10) Patent No.: US 10,973,753 B2
(45) Date of Patent: *Apr. 13, 2021

(54) DISPERSION OF POLYMER PARTICLES IN A NON-AQUEOUS MEDIUM AND COSMETIC USE THEREOF

(71) Applicant: L'OREAL, Paris (FR)

(72) Inventors: Julien Portal, Les Pavillions sous Bois (FR); Xavier Schultze, Les Pavillons sous Bois (FR); Simon Taupin, Anthony (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/538,319

(22) PCT Filed: Dec. 10, 2015

(86) PCT No.: PCT/EP2015/079265
§ 371 (c)(1),
(2) Date: Jun. 21, 2017

(87) PCT Pub. No.: WO2016/102191
PCT Pub. Date: Jun. 30, 2016

(65) Prior Publication Data
US 2017/0367966 A1    Dec. 28, 2017

(30) Foreign Application Priority Data
Dec. 22, 2014  (FR) ...................... 1463082

(51) Int. Cl.
| | | |
|---|---|---|
| *A61K 8/891* | (2006.01) | |
| *A61Q 1/08* | (2006.01) | |
| *A61K 8/31* | (2006.01) | |
| *A61K 8/04* | (2006.01) | |
| *A61K 8/81* | (2006.01) | |
| *A61Q 1/10* | (2006.01) | |
| *A61Q 1/04* | (2006.01) | |
| *A61Q 1/02* | (2006.01) | |

(52) U.S. Cl.
CPC ............. *A61K 8/891* (2013.01); *A61K 8/044* (2013.01); *A61K 8/31* (2013.01); *A61K 8/8164* (2013.01); *A61Q 1/02* (2013.01); *A61Q 1/04* (2013.01); *A61Q 1/08* (2013.01); *A61Q 1/10* (2013.01); *A61K 2800/52* (2013.01); *A61K 2800/594* (2013.01); *A61K 2800/614* (2013.01); *A61K 2800/654* (2013.01)

(58) Field of Classification Search
CPC ...... A61K 8/31; A61K 2800/654; A61Q 1/02; A61Q 1/04; A61Q 1/08; A61Q 1/10
See application file for complete search history.

(56) References Cited

U.S. PATENT DOCUMENTS

| | | | | |
|---|---|---|---|---|
| 5,945,095 A | * | 8/1999 | Mougin | A61K 8/04 424/450 |
| 6,630,133 B1 | | 10/2003 | Dupuis | |
| 2011/0243864 A1 | * | 10/2011 | Farcet | A61K 8/04 424/61 |

FOREIGN PATENT DOCUMENTS

| | | |
|---|---|---|
| EP | 0 749 747 A1 | 12/1996 |
| FR | 2 880 267 A1 | 7/2006 |
| FR | 2 972 630 A1 | 9/2012 |
| FR | 2 972 631 A1 | 9/2012 |

OTHER PUBLICATIONS

Polymer Properties Database, retrieved from https://polymerdatabase.com/polymer%20chemistry/Ideal%20Copolymers.html on Nov. 19, 2020. (Year: 2020).*

"Rouge d'Armani Lasting Satin Lip Color", GNPD Mintel, Mar. 2011.

* cited by examiner

*Primary Examiner* — Jianfeng Song
(74) *Attorney, Agent, or Firm* — Polsinelli PC

(57) ABSTRACT

The invention relates to a dispersion of polymer particles stabilized with a stabilizer in a nonaqueous medium containing at least one hydrocarbon-based oil, the polymer of the particles being a $C_1$-$C_4$ alkyl (meth)acrylate polymer; the stabilizer being a $C_1$-$C_4$ alkyl (meth)acrylate polymer and optionally of a silicone macromonomer (I):

the stabilizer being a polymer comprising from 50% to 100% by weight, relative to the total weight of the stabilizer, of $C_8$-$C_{22}$ alkyl acrylate, from 0 to 50% by weight of $C_1$-$C_4$ alkyl (meth)acrylate and optionally silicone macromonomer (I).

The invention also relates to the composition comprising said dispersion of polymer particles.

Cosmetic use for caring for and making up keratin materials.

22 Claims, No Drawings

DISPERSION OF POLYMER PARTICLES IN A NON-AQUEOUS MEDIUM AND COSMETIC USE THEREOF

The present invention relates to a dispersion of polymer particles dispersed in a nonaqueous medium, and also to a cosmetic composition comprising such a dispersion.

It is known practice to use in cosmetics dispersions of polymer particles, in organic media such as hydrocarbon-based oils, for instance hydrocarbons. Polymers are especially used as film-forming agents in makeup products such as mascaras, eyeliners, eyeshadows or lipsticks.

Document EP-A-749 747 describes in the examples dispersions in hydrocarbon-based oils (liquid paraffin, isododecane) of acrylic polymers stabilized with polystyrene/copoly (ethylene-propylene) diblock copolymers. However, when the solids (polymer+stabilizer) content exceeds 25% by weight, the dispersion then becomes too viscous, thus giving rise to formulation difficulties in cosmetic products on account of a large change in the viscosity of the final composition of these products. In addition, the film obtained after application of the dispersion to the skin is slightly glossy.

Document WO-A-2010/046 229 describes dispersions in isododecane of acrylic polymers stabilized with block and especially triblock stabilizing polymers of acrylic monomers. In the examples, according to Example 1A, the stabilizing polymer is prepared by reversible chain-transfer controlled radical polymerization. This polymerization method is difficult to perform on an industrial scale since it requires a large number of intermediate purification steps to obtain the final polymer dispersion.

Moreover, dispersions of acrylic polymers in isododecane may have problems of compatibility with silicone oils, giving rise to phase separation of the dispersion. There is thus a need for a stable dispersion of acrylic polymer stabilized in a nonaqueous medium comprising a hydrocarbon-based oil, which is easy to manufacture industrially, and which makes it possible to obtain a film that has good cosmetic properties, especially good gloss, and which is also compatible with silicone oils.

The Applicant has discovered that novel dispersions of $C_1$-$C_4$ alkyl (meth)acrylate polymer particles stabilized with a particular stabilizer based on a $C_8$-$C_{22}$ alkyl acrylate polymer, the polymer and/or the stabilizer comprising a particular silicone macromonomer, in a hydrocarbon-based oil have good stability, especially after storage for seven days at room temperature (25° C.), are easy to manufacture industrially without using a large number of synthetic steps and also make it possible to obtain a film after application to a support which has good cosmetic properties, in particular good gloss and good resistance to oils. These dispersions also have good compatibility with silicone oils, in particular when the dispersion medium comprises up to 25% by weight of silicone oil, relative to the total weight of oils present in the dispersion.

One subject of the present invention is thus a dispersion of particles of at least one polymer stabilized with a stabilizer in a nonaqueous medium containing at least one hydrocarbon-based oil, the polymer of the particles being a polymer of $C_1$-$C_4$ alkyl (meth)acrylate and optionally of a silicone macromonomer (I) as defined hereinbelow; the stabilizer being a polymer comprising from 50% to 100% by weight of $C_8$-$C_{22}$ alkyl acrylate, from 0 to 50% by weight of $C_1$-$C_4$ alkyl (meth)acrylate and optionally a silicone macromonomer (I) as defined hereinbelow, relative to the total weight of the stabilizer, the stabilizer and/or the polymer of the particles comprising at least the silicone macromonomer (I), and:

(i) when the stabilizer comprises the silicone macromonomer (I), the macromonomer is present in the stabilizer in a content of less than or equal to 5.5% by weight, relative to the total weight of the combination of stabilizer+polymer of the particles; the polymer of the particles optionally comprising said silicone macromonomer (I) in a content of less than or equal to 28% by weight, relative to the total weight of the combination of stabilizer+polymer of the particles;

(ii) when the polymer of the particles comprises the silicone macromonomer (I) and the stabilizer does not comprise silicone macromonomer (I), the macromonomer is present in a content of less than or equal to 18% by weight, relative to the total weight of the combination of stabilizer+polymer of the particles.

The presence of the silicone macromonomer (I) in the stabilizer and/or the polymer of the particles makes it possible to obtain a polymer dispersion that is stable, in particular after storage for 7 days at room temperature (25° C.).

Another subject of the invention is a composition comprising, in a physiologically acceptable medium, a polymer particle dispersion as defined previously.

A subject of the invention is also a process for the nontherapeutic cosmetic treatment of keratin materials, comprising the application to the keratin materials of a composition as defined previously. The treatment process is in particular a process for caring for or making up keratin materials.

The dispersions according to the invention are thus constituted of particles, which are generally spherical, of at least one polymer in a nonaqueous medium.

The polymer of the particles is a $C_1$-$C_4$ alkyl (meth)acrylate polymer.

The $C_1$-$C_4$ alkyl (meth)acrylate monomers may be chosen from methyl (meth)acrylate, ethyl (meth)acrylate, n-propyl (meth)acrylate, isopropyl (meth)acrylate, n-butyl (meth)acrylate and tert-butyl (meth)acrylate.

A $C_1$-$C_4$ alkyl acrylate monomer is advantageously used. Preferentially, the polymer of the particles is a methyl acrylate and/or ethyl acrylate polymer.

The polymer of the particles and/or the stabilizer may comprise a polydimethylsiloxane macromonomer comprising a monoacryloyloxy or monomethacryloyloxy end group of formula (I) (subsequently referred to as silicone macromonomer) below:

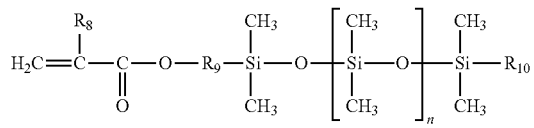

in which:
R8 denotes a hydrogen atom or a methyl group; preferably methyl;
R9 denotes a linear or branched, preferably linear, divalent hydrocarbon-based group containing from 1 to 10 carbon atoms, preferably containing from 2 to 4 carbon atoms, and optionally containing one or two —O— ether bonds; preferably an ethylene, propylene or butylene group;

R10 denotes a linear or branched alkyl group containing from 1 to 10 carbon atoms, especially from 2 to 8 carbon atoms; preferably methyl, ethyl, propyl, butyl or pentyl;

n denotes an integer ranging from 1 to 300, preferably ranging from 3 to 200 and preferentially ranging from 5 to 100.

Use may in particular be made of monomethacryloyloxypropyl polydimethylsiloxanes such as those sold under the names MCR-M07, MCR-M17, MCR-M11 and MCR-M22 by Gelest Inc or X-22-2475, X-22-2426 and X-22-174DX by Shin Etsu.

The polymer of the particles may also comprise an ethylenically unsaturated acid monomer or the anhydride thereof, especially chosen from ethylenically unsaturated acid monomers comprising at least one carboxylic, phosphoric or sulfonic acid function, such as crotonic acid, itaconic acid, fumaric acid, maleic acid, maleic anhydride, styrenesulfonic acid, vinylbenzoic acid, vinylphosphoric acid, acrylic acid, methacrylic acid, acrylamidopropanesulfonic acid or acrylamidoglycolic acid, and salts thereof.

Preferably, the ethylenically unsaturated acid monomer is chosen from (meth)acrylic acid, maleic acid and maleic anhydride.

The salts may be chosen from salts of alkali metals, for example sodium or potassium; salts of alkaline-earth metals, for example calcium, magnesium or strontium; metal salts, for example zinc, aluminum, manganese or copper; ammonium salts of formula $NH_4^+$; quaternary ammonium salts; salts of organic amines, for instance salts of methylamine, dimethylamine, trimethylamine, triethylamine, ethylamine, 2-hydroxyethylamine, bis(2-hydroxyethyl)amine or tris(2-hydroxyethyl)amine; lysine or arginine salts.

The polymer of the particles may thus comprise, or be essentially constituted of,
from 62% to 100% by weight of $C_1$-$C_4$ alkyl (meth)acrylate and from 0 to 38% by weight of the silicone macromonomer (I)
and from 0 to 20% by weight of ethylenically unsaturated acid monomer, relative to the total weight of the polymer.

According to a first embodiment of the invention, the polymer consists essentially of a polymer of one or more $C_1$-$C_4$ alkyl (meth)acrylate monomers.

According to a second embodiment of the invention, the polymer consists essentially of a copolymer of $C_1$-$C_4$ (meth)acrylate and of (meth)acrylic acid or maleic anhydride.

According to a third embodiment, the polymer is essentially constituted of a copolymer of $C_1$-$C_4$ (meth)acrylate and of silicone macromonomer (I).

According to a fourth embodiment of the invention, the polymer is essentially constituted of a copolymer of $C_1$-$C_4$ (meth)acrylate, of (meth)acrylic acid or maleic anhydride and of silicone macromonomer (I).

The polymer of the particles may be chosen from:
methyl acrylate homopolymers
methyl acrylate/silicone macromonomer (I) copolymers
ethyl acrylate homopolymers
ethyl acrylate/silicone macromonomer (I) copolymers
methyl acrylate/ethyl acrylate copolymers
methyl acrylate/ethyl acrylate/silicone macromonomer (I) copolymers
methyl acrylate/ethyl acrylate/acrylic acid copolymers
methyl acrylate/ethyl acrylate/acrylic acid/silicone macromonomer (I) copolymers
methyl acrylate/ethyl acrylate/maleic anhydride copolymers
methyl acrylate/ethyl acrylate/maleic anhydride/silicone macromonomer (I) copolymers
methyl acrylate/acrylic acid copolymers
methyl acrylate/acrylic acid/silicone macromonomer (I) copolymers
ethyl acrylate/acrylic acid copolymers
ethyl acrylate/acrylic acid/silicone macromonomer (I) copolymers
methyl acrylate/maleic anhydride copolymers
methyl acrylate/maleic anhydride/silicone macromonomer (I) copolymers
ethyl acrylate/maleic anhydride/silicone macromonomer (I) copolymers
ethyl acrylate/maleic anhydride copolymers;
and preferably from:
methyl acrylate/acrylate copolymers
methyl acrylate/ethyl acrylate/silicone macromonomer (I) copolymers
methyl acrylate/ethyl acrylate/acrylic acid copolymers.

Advantageously, the polymer of the particles is a non-crosslinked polymer.

The polymer of the particles of the dispersion preferably has a number-average molecular weight ranging from 2000 to 10 000 000 and preferably ranging from 150 000 to 500 000.

The polymer of the particles may be present in the dispersion in a content ranging from 20% to 60% by weight, relative to the total weight of the dispersion.

The stabilizer is a polymer comprising from 50% to 100% by weight, preferably from 60% to 95% by weight, of $C_8$-$C_{22}$ alkyl acrylate, from 0 to 50% by weight, preferably from 5% to 40% by weight, of $C_1$-$C_4$ alkyl (meth)acrylate and optionally the silicone macromonomer (I) as described previously. The stabilizer is preferably a statistical polymer.

The $C_8$-$C_{22}$ alkyl acrylate may comprise a linear, branched or cyclic alkyl group, for instance a 2-ethylhexyl, isobornyl, lauryl, behenyl or stearyl group.

Preferably, isobornyl acrylate and 2-ethylhexyl acrylate are used. Isobornyl acrylate is preferentially used.

Advantageously, the stabilizer is chosen from:
2-ethylhexyl acrylate homopolymers
isobornyl acrylate homopolymers
isobornyl acrylate/methyl acrylate copolymers
2-ethylhexyl acrylate/methyl acrylate copolymers
isobornyl acrylate/methyl acrylate/ethyl acrylate copolymers
2-ethylhexyl acrylate/methyl acrylate/ethyl acrylate copolymers
isobornyl acrylate/methyl acrylate/ethyl acrylate/silicone macromonomer (I) copolymers
2-ethylhexyl acrylate/methyl acrylate/ethyl acrylate/silicone macromonomer (I) copolymers.

The stabilizing polymer preferably has a number-average molecular weight ranging from 10 000 to 400 000 and preferably ranging from 20 000 to 200 000.

The stabilizer is in contact with the surface of the polymer particles and thus makes it possible to stabilize these particles at the surface in order to keep these particles in dispersion in the nonaqueous medium of the dispersion. Thus, the polymer particles are surface-stabilized by the stabilizer. The stabilizer is a polymer distinct from the polymer of the particles: the stabilizer does not form a covalent bond with the polymer of the particles.

According to a first embodiment according to the invention, the silicone macromonomer (I) is present in the stabilizer of the dispersion; it is not present in the polymer of the particles.

The silicone macromonomer (I) is present in the stabilizer in a content of less than or equal to 5.5% by weight, in particular ranging from 0.1% to 5.5% by weight, relative to the total weight of the combination of stabilizer+polymer of the particles.

In particular, the silicone macromonomer (I) may be present in the stabilizer in a content ranging from 0.1% to 35% by weight, relative to the total weight of the stabilizer.

Advantageously, the combination of stabilizer+polymer of the particles present in the dispersion comprises from 5% to 50% by weight of polymerized $C_8$-$C_{22}$ alkyl acrylate, from 44.5% to 89.5% by weight of polymerized $C_1$-$C_4$ alkyl (meth)acrylate and from 0.1% to 5.5% by weight of silicone macromonomer (I), relative to the total weight of the combination of stabilizer+polymer of the particles.

Preferentially, the combination of stabilizer+polymer of the particles present in the dispersion comprises from 6% to 30% by weight of polymerized $C_8$-$C_{22}$ alkyl acrylate, from 64.5% to 93.9% by weight of polymerized $C_1$-$C_4$ alkyl (meth)acrylate and from 0.1% to 5.5% by weight of silicone macromonomer (I), relative to the total weight of the combination of stabilizer+polymer of the particles.

According to a second embodiment according to the invention, the silicone macromonomer (I) is present in the stabilizer of the dispersion and in the polymer of the particles.

The silicone macromonomer (I) is present in the stabilizer in a content of less than or equal to 5.5% by weight, in particular ranging from 0.1% to 5.5% by weight, relative to the total weight of the combination of stabilizer+polymer of the particles; and it is present in the polymer of the particles in a content of less than or equal to 28% by weight, in particular ranging from 0.1% to 28% by weight, relative to the total weight of the combination of stabilizer+polymer of the particles.

In particular, the silicone macromonomer (I) may be present in the stabilizer in a content ranging from 0.1% to 35% by weight, relative to the total weight of the stabilizer; and it may be present in the polymer of the particles in a content ranging from 0.1% to 38% by weight, relative to the total weight of the polymer of the particles.

Advantageously, the combination of stabilizer+polymer of the particles present in the dispersion comprises from 5% to 50% by weight of polymerized $C_8$-$C_{22}$ alkyl acrylate, from 16.5% to 94.9% by weight of polymerized $C_1$-$C_4$ alkyl (meth)acrylate and from 0.1% to 33.5% by weight of silicone macromonomer (I), relative to the total weight of the combination of stabilizer+polymer of the particles.

Preferentially, the combination of stabilizer+polymer of the particles present in the dispersion comprises from 6% to 30% by weight of polymerized $C_8$-$C_{22}$ alkyl acrylate, from 36.5% to 93.9% by weight of polymerized $C_1$-$C_4$ alkyl (meth)acrylate and from 0.1% to 33.5% by weight of silicone macromonomer (I), relative to the total weight of the combination of stabilizer+polymer of the particles.

According to a third embodiment according to the invention, the silicone macromonomer (I) is present in the polymer of the particles of the dispersion; it is not present in the stabilizer.

The silicone macromonomer (I) is present in the polymer of the particles in a content of less than or equal to 18% by weight, in particular ranging from 0.1% to 18% by weight, relative to the total weight of the combination of stabilizer+polymer of the particles. Advantageously, the silicone macromonomer (I) is present in an amount ranging from 0.1% to 25% by weight, relative to the total weight of the polymer of the particles.

Advantageously, the combination of stabilizer+polymer of the particles present in the dispersion comprises from 5% to 50% by weight of polymerized $C_8$-$C_{22}$ alkyl acrylate, from 32% to 94.9% by weight of polymerized $C_1$-$C_4$ alkyl (meth)acrylate and from 0.1% to 18% by weight of silicone macromonomer (I), relative to the total weight of the combination of stabilizer+polymer of the particles.

Preferentially, the combination of stabilizer+polymer of the particles present in the dispersion comprises from 6% to 30% by weight of polymerized $C_8$-$C_{22}$ alkyl acrylate, from 52% to 93.9% by weight of polymerized $C_1$-$C_4$ alkyl (meth) acrylate and from 0.1% to 18% by weight of silicone macromonomer (I), relative to the total weight of the combination of stabilizer+polymer of the particles.

The oily medium of the polymer dispersion comprises a hydrocarbon-based oil. The hydrocarbon-based oil is an oil that is liquid at room temperature (25° C.).

The term "hydrocarbon-based oil" means an oil formed essentially from, or even constituted by, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be chosen from:
hydrocarbon-based oils containing from 8 to 16 carbon atoms, and especially:
branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade names Isopar or Permethyl,
linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in examples 1 and 2 of patent application WO 2008/155 059 from the company Cognis, and mixtures thereof.
short-chain esters (containing from 3 to 8 carbon atoms in total) such as ethyl acetate, methyl acetate, propyl acetate or n-butyl acetate,
hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or else wheatgerm oil, sunflower oil, grapeseed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, rapeseed oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by Dynamit Nobel;
synthetic ethers containing from 10 to 40 carbon atoms;
linear or branched hydrocarbons of mineral or synthetic origin, such as petroleum jelly, polydecenes, hydrogenated polyisobutene such as Parleam®, squalane and liquid paraffins, and mixtures thereof,
synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alcohol benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alcohol or polyalcohol heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Advantageously, the hydrocarbon-based oil is apolar (thus formed solely from carbon and hydrogen atoms).

The hydrocarbon-based oil is preferably chosen from hydrocarbon-based oils containing from 8 to 16 carbon atoms, in particular the apolar oils described previously.

Preferentially, the hydrocarbon-based oil is isododecane.

The polymer particles of the dispersion preferably have an average size, in particular a number-average size, ranging from 50 to 500 nm, especially ranging from 75 to 400 nm and better still ranging from 100 to 250 nm.

In general, the dispersion according to the invention may be prepared in the following manner, which is given as an example.

The polymerization may be performed in dispersion, i.e. by precipitation of the polymer during formation, with protection of the formed particles with a stabilizer.

In a first step, the stabilizing polymer is prepared by mixing the constituent monomer(s) of the stabilizing polymer with a free-radical initiator, in a solvent known as the synthesis solvent, and by polymerizing these monomers. In a second step, the constituent monomer(s) of the polymer of the particles are added to the stabilizing polymer formed and polymerization of these added monomers is performed in the presence of the free-radical initiator.

When the nonaqueous medium is a nonvolatile hydrocarbon-based oil, the polymerization may be performed in an apolar organic solvent (synthesis solvent), followed by adding the nonvolatile hydrocarbon-based oil (which should be miscible with said synthesis solvent) and selectively distilling off the synthesis solvent.

A synthesis solvent which is such that the monomers of the stabilizing polymer and the free-radical initiator are soluble therein, and the polymer particles obtained are insoluble therein, so that they precipitate therein during their formation, is thus chosen.

In particular, the synthesis solvent may be chosen from alkanes such as heptane or cyclohexane.

When the nonaqueous medium is a volatile hydrocarbon-based oil, the polymerization may be performed directly in said oil, which thus also acts as synthesis solvent. The monomers should also be soluble therein, as should the free-radical initiator, and the polymer of the particles which is obtained should be insoluble therein.

The monomers are preferably present in the synthesis solvent, before polymerization, in a proportion of 5-20% by weight. The total amount of the monomers may be present in the solvent before the start of the reaction, or part of the monomers may be added gradually as the polymerization reaction proceeds.

The free-radical initiator may especially be azobisisobutyronitrile or tert-butyl peroxy-2-ethylhexanoate.

The polymerization may be performed at a temperature ranging from 70 to 110° C.

The polymer particles are surface-stabilized, when they are formed during the polymerization, by means of the stabilizer.

The stabilization may be performed by any known means, and in particular by direct addition of the stabilizer, during the polymerization.

The stabilizer is preferably also present in the mixture before polymerization of the monomers of the polymer of the particles. However, it is also possible to add it continuously, especially when the monomers of the polymer of the particles are also added continuously.

From 10% to 30% by weight and preferably from 15% to 25% by weight of stabilizer may be used relative to the total weight of monomers used (stabilizer+polymer of the particles).

The polymer dispersion obtained according to the invention may be used in a composition comprising a physiologically acceptable medium, in particular in a cosmetic composition.

The term "physiologically acceptable medium" means a medium that is compatible with human keratin materials, for instance the skin, the lips, the nails, the eyelashes, the eyebrows or the hair.

The term "cosmetic composition" means a composition that is compatible with keratin materials, which has a pleasant color, odor and feel and which does not cause unacceptable discomfort (stinging, tautness or redness) liable to discourage the consumer from using it.

The term "keratin materials" means the skin (body, face, contour of the eyes, scalp), head hair, eyelashes, eyebrows, bodily hairs, nails or lips.

The composition according to the invention may comprise a cosmetic additive chosen from water, fragrances, preserving agents, fillers, dyestuffs, UV-screening agents, oils, waxes, surfactants, moisturizers, vitamins, ceramides, antioxidants, free-radical scavengers, polymers and thickeners.

In particular, the composition may comprise a silicone oil, which may be chosen from linear or cyclic volatile silicone oils, especially containing from 2 to 10 silicon atoms, preferably from 2 to 7 silicon atoms, these silicones optionally comprising alkyl or alkoxy groups containing from 1 to 10 carbon atoms, for instance octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane or dodecamethylpentasiloxane;

polydimethylsiloxanes (PDMSs) comprising alkyl or alkoxy groups, that are pendent and/or at the end of a silicone chain, the groups each containing from 2 to 60 carbon atoms, especially $(C_2-C_{60})$alkyl dimethicones; $(C_2-C_{60})$ alkyl methicones; phenyl silicones, for instance phenyl trimethicones, phenyl dimethicones, phenyltrimethylsiloxydiphenylsiloxanes, diphenyl dimethicones, trimethylsiloxyphenyl dimethicones and diphenylmethyldiphenyltrisiloxanes;

and mixtures thereof.

The silicone oil may be present in the composition according to the invention in a content ranging from 0.1% to 60% by weight, relative to the total weight of the composition, preferably ranging from 1% to 50% by weight and better still ranging from 1% to 40% by weight.

The composition according to the invention may comprise the polymer of the dispersion in a content ranging from 1% to 50% by weight and preferably ranging from 10% to 45% by weight relative to the total weight of the composition.

Advantageously, the composition according to the invention is a makeup composition, in particular a lip makeup composition, a mascara, an eyeliner, an eyeshadow or a foundation.

According to one embodiment, the composition according to the invention is an anhydrous composition. The term "anhydrous composition" means a composition containing less than 2% by weight of water, or even less than 0.5% of water, and is especially free of water. If appropriate, such small amounts of water may in particular be introduced by ingredients of the composition which may contain residual amounts thereof.

The composition according to the invention may be an aerosol composition also containing a propellant.

Propellants that may be used include liquefied gases such as dimethyl ether, chlorinated and/or fluorinated hydrocarbons such as trichlorofluoromethane, dichlorodifluoromethane, chlorodifluoromethane, 1,1,1,2-tetrafluoroethane, chloropentafluoroethane, 1-chloro-1,1-difluoroethane or 1,1-difluoroethane, or volatile hydrocarbons especially such as $C_{3-5}$ alkanes, for instance propane, isopropane, n-butane, isobutane or pentane, or compressed gases such as air, nitrogen, carbon dioxide, and mixtures thereof.

Use may preferably be made of dimethyl ether, 1,1,1,2-tetrafluoroethane and $C_{3-5}$ alkanes and in particular propane, n-butane and isobutane, and mixtures thereof.

Isobutane is preferentially used.

The aerosol composition is generally packaged, in a known manner, in an aerosol device comprising a container and a means for dispensing the composition. The dispensing means generally comprises a dispensing valve controlled by a dispensing head, which may comprise a nozzle via which the aerosol composition is vaporized. A person skilled in the art in the field of aerosols is entirely capable of determining the characteristics of the packaging that is suitable for dispensing the composition in the form of an aerosol spray.

The propellant may be present in the composition in a content ranging from 1% to 95% by weight, preferably from 1.5% to 50% by weight and better still from 2% to 30% by weight, relative to the total weight of the composition.

As shown by the examples, the oily dispersion according to the invention has good compatibility with isobutane, especially in the presence of polydimethylsiloxane silicone oil.

The invention is illustrated in greater detail in the following examples. The amounts are expressed as weight percentages.

Evaluation of the Cosmetic Properties of the Oily Dispersions:

The oily dispersion to be evaluated was placed on a contrast card (for example that sold under the reference Byko-charts by the company Byk-Gardner) and the film deposited was dried for 24 hours at room temperature (25° C.). The dry film has a thickness of about 50 μm.

The gloss of the film was measured using a glossmeter (three angles Refo 3/Refo 3D from Labomat) at an angle of 20°.

The resistance of the film to the fatty substance was determined by depositing on the dry film three drops of olive oil onto the black part of the contrast card. The drops were left in contact with the dry film for 10 minutes, 30 minutes and 60 minutes, respectively, and the oil drop was then wiped and the appearance of the area of the film that was in contact with the oil was observed. If the film was damaged by the oil drop, the polymer film is considered as not being resistant to olive oil.

The tacky aspect of the polymer film was evaluated by touching the dry film with a finger.

All the percentages of reagents described in the examples are weight percentages.

EXAMPLE 1

In a first step, 120 g of isododecane, 50 g of isobornyl acrylate, 2 g of methyl acrylate, 2 g of ethyl acrylate, 12.5 g of polydimethylsiloxane methacrylate (X-22-2426 from Shin-Etsu) and 0.665 g of tert-butyl peroxy-2-ethylhexanoate (Trigonox 21S from Akzo) were placed in a reactor. The isobornyl acrylate/methyl acrylate/ethyl acrylate/PDMS methacrylate weight ratio is 75.2/3/3/18.8.

The mixture was heated to 90° C. under argon with stirring.

After 2 hours of reaction, 78 g of isododecane were added to the reactor feedstock and the mixture was heated to 90° C.

In a second step, a mixture of 91.5 g of methyl acrylate, 91.5 g of ethyl acrylate, 183 g of isododecane and 1.83 g of Trigonox 21S were run in over the course of one hour, and the mixture was left to react for 7 hours. 0.3 liter of isododecane were then added and part of the isododecane was evaporated off to obtain a solids content of 45% by weight.

A dispersion of particles of methyl acrylate/ethyl acrylate (50/50 by weight) copolymer, stabilized with a statistical copolymer stabilizer containing 75.2% by weight of isobornyl acrylate, 3% of methyl acrylate, 3% of ethyl acrylate and 18.8% of PDMS methacrylate, in isododecane, was obtained.

The oily dispersion contains in total (stabilizer+particles) 20% of isobornyl acrylate, 37.5% of methyl acrylate, 37.5% of ethyl acrylate and 5% of PDMS methacrylate.

The particles of the polymer of the dispersion have a number-average size of between about 170 nm and 200 nm.

The dispersion is stable after storage for 7 days at room temperature (25° C.).

The film obtained with the oily dispersion has the following properties:

| Gloss at 20° | Resistance to fatty substances | Tackiness |
| --- | --- | --- |
| 73 | Resistant to fatty substances | Non-tacky |

EXAMPLE 2

A dispersion of polymer particles in isododecane was prepared according to the procedure of example 1, using:
Step 1: 50 g of isobornyl acrylate, 2 g of methyl acrylate, 2 g of ethyl acrylate, 0.54 g of Trigonox 21S, 120 g of isododecane; followed by addition, after reaction, of 78 g of isododecane.
Step 2: 98 g of methyl acrylate, 73 g of ethyl acrylate, 25 g of polydimethylsiloxane methacrylate (X-22-2426 from Shin-Etsu), 1.96 g of Trigonox 21S, 196 g of isododecane.
After reaction, addition of 0.3 liter of isododecane and evaporation to obtain a solids content of 40% by weight.

A dispersion in isododecane of methyl acrylate/ethyl acrylate/PDMS acrylate (50/37.2/12.8) copolymer particles stabilized with an isobornyl acrylate/methyl acrylate/ethyl acrylate (92.6/3.7/3.7) statistical copolymer was obtained.

The oily dispersion contains in total (stabilizer+particles) 20% of isobornyl acrylate, 40% of methyl acrylate, 30% of ethyl acrylate and 10% of PDMS methacrylate.

The particles of the polymer of the dispersion have a number-average size of between about 170 nm and 200 nm.

The dispersion is stable after storage for 7 days at room temperature (25° C.).

The film obtained with the oily dispersion has the following properties:

| Gloss at 20° | Resistance to fatty substances | Tackiness |
|---|---|---|
| 60 | Resistant to fatty substances | Non-tacky |

EXAMPLE 3

A dispersion of polymer particles in isododecane was prepared according to the procedure of example 1, using:
Step 1: 50 g of isobornyl acrylate, 2 g of methyl acrylate, 2 g of ethyl acrylate, 12.5 g of polydimethylsiloxane methacrylate (X-22-2426 from Shin-Etsu), 0.665 g of Trigonox 21S, 120 g of isododecane; followed by addition, after reaction, of 78 g of isododecane.
Step 2: 91.5 g of methyl acrylate, 79 g of ethyl acrylate, 12.5 g of polydimethylsiloxane methacrylate (X-22-2426 from Shin-Etsu), 1.83 g of Trigonox 21S, 183 g of isododecane. After reaction, addition of 0.3 liter of isododecane and evaporation to obtain a solids content of 42% by weight.

A dispersion in isododecane of methyl acrylate/ethyl acrylate/PDMS acrylate (50/43.2/6.8) copolymer particles stabilized with an isobornyl acrylate/methyl acrylate/ethyl acrylate/PDMS methacrylate (75.2/3/3/18.8) statistical copolymer was obtained.

The oily dispersion contains in total (stabilizer+particles) 20% of isobornyl acrylate, 37.5% of methyl acrylate, 32.5% of ethyl acrylate and 10% of PDMS methacrylate.

The dispersion is stable after storage for 7 days at room temperature (25° C.).

The film obtained with the oily dispersion has the following properties:

| Gloss at 20° | Resistance to fatty substances | Tackiness |
|---|---|---|
| 74 | Resistant to fatty substances | Non-tacky |

EXAMPLE 4

A dispersion of polymer particles in isododecane was prepared according to the procedure of example 1, using:
Step 1: 50 g of isobornyl acrylate, 2 g of methyl acrylate, 2 g of ethyl acrylate, 12.5 g of polydimethylsiloxane methacrylate (X-22-2426 from Shin-Etsu), 0.665 g of Trigonox 21S, 72 g of isododecane and 48 g of ethyl acetate; followed by addition, after reaction, of 47 g of isododecane and 31 g of ethyl acetate.
Step 2: 23 g of methyl acrylate, 135.5 g of ethyl acrylate, 1.835 g of Trigonox 21S, 183.5 g of isododecane. After reaction, addition of 0.3 liter of an isododecane/ethyl acetate mixture (60/40 weight/weight) and total evaporation of the ethyl acetate and partial evaporation of the isododecane to obtain a solids content of 53% by weight.

A dispersion in isododecane of methyl acrylate/ethyl acrylate/acrylic acid (12.5/73.9/13.6) copolymer particles stabilized with an isobornyl acrylate/methyl acrylate/ethyl acrylate/PDMS methacrylate (75.2/3/3/18.8) statistical copolymer was obtained.

The oily dispersion contains in total (stabilizer+particles) 20% of isobornyl acrylate, 10% of methyl acrylate, 55% of ethyl acrylate, 10% of acrylic acid and 5% of PDMS methacrylate.

The dispersion is stable after storage for 7 days at room temperature (25° C.).

The film obtained with the oily dispersion has the following properties:

| Gloss at 20° | Resistance to fatty substances | Tackiness |
|---|---|---|
| 67 | Resistant to fatty substances | Non-tacky |

EXAMPLE 5

A dispersion of polymer particles in isododecane was prepared according to the procedure of example 1, using:
Step 1: 25 g of 2-ethylhexyl acrylate, 2 g of methyl acrylate, 2 g of ethyl acrylate, 12.5 g of polydimethylsiloxane methacrylate (X-22-2426 from Shin-Etsu), 0.415 g of Trigonox 21S, 120 g of isododecane; followed by addition, after reaction, of 78 g of isododecane.
Step 2: 104 g of methyl acrylate, 104 g of ethyl acrylate, 2.08 g of Trigonox 21S, 208 g of isododecane. After reaction, addition of 0.3 liter of isododecane and evaporation to obtain a solids content of 45% by weight.

A dispersion in isododecane of methyl acrylate/ethyl acrylate (50/50) copolymer particles stabilized with a 2-ethylhexyl acrylate/methyl acrylate/ethyl acrylate/PDMS methacrylate (60.3/4.8/4.8/30.1) statistical copolymer was obtained.

The oily dispersion contains in total (stabilizer+particles) 10% of 2-ethylhexyl acrylate, 42.5% of methyl acrylate, 42.5% of ethyl acrylate and 5% of PDMS methacrylate.

The dispersion is stable after storage for 7 days at room temperature (25° C.).

The film obtained with the oily dispersion has the following properties:

| Gloss at 20° | Resistance to fatty substances | Tackiness |
|---|---|---|
| 51 | Resistant to fatty substances | Tackiness |

EXAMPLE 6

A dispersion of polymer particles in isododecane was prepared according to the procedure of example 1, using:
Step 1: 25 g of 2-ethylhexyl acrylate, 2 g of methyl acrylate, 2 g of ethyl acrylate, 0.29 g of Trigonox 21S, 120 g of isododecane; followed by addition, after reaction, of 78 g of isododecane.
Step 2: 110.5 g of methyl acrylate, 85.5 g of ethyl acrylate, 25 g of polydimethylsiloxane methacrylate (X-22-2426 from Shin-Etsu), 2.21 g of Trigonox 21S, 221 g of isododecane. After reaction, addition of 0.3 liter of isododecane and evaporation to obtain a solids content of 43% by weight.

A dispersion in isododecane of methyl acrylate/ethyl acrylate/PDMS acrylate (50/38.7/11.3) copolymer particles stabilized with a 2-ethylhexyl acrylate/methyl acrylate/ethyl acrylate (86.2/6.9/6.9) statistical copolymer was obtained.

The oily dispersion contains in total (stabilizer+particles) 10% of 2-ethylhexyl acrylate, 45% of methyl acrylate, 35% of ethyl acrylate and 10% of PDMS methacrylate.

The dispersion is stable after storage for 7 days at room temperature (25° C.).

The film obtained with the oily dispersion has the following properties:

| Gloss at 20° | Resistance to fatty substances | Tackiness |
|---|---|---|
| 63 | Resistant to fatty substances | Tackiness |

EXAMPLE 7

A dispersion of polymer particles in isododecane was prepared according to the procedure of example 1, using:

Step 1: 25 g of 2-ethylhexyl acrylate, 2 g of methyl acrylate, 2 g of ethyl acrylate, 12.5 g of polydimethylsiloxane methacrylate (X-22-2426 from Shin-Etsu), 0.415 g of Trigonox 21S, 120 g of isododecane; followed by addition, after reaction, of 78 g of isododecane.

Step 2: 104 g of methyl acrylate, 91.5 g of ethyl acrylate, 12.5 g of polydimethylsiloxane methacrylate (X-22-2426 from Shin-Etsu), 2.08 g of Trigonox 21S, 208 g of isododecane. After reaction, addition of 0.3 liter of isododecane and evaporation to obtain a solids content of 46% by weight.

A dispersion in isododecane of methyl acrylate/ethyl acrylate/PDMS acrylate (50/44/6) copolymer particles stabilized with a 2-ethylhexyl acrylate/methyl acrylate/ethyl acrylate/PDMS methacrylate (60.2/4.8/4.8/30.2) statistical copolymer was obtained.

The oily dispersion contains in total (stabilizer+particles) 10% of 2-ethylhexyl acrylate, 42.5% of methyl acrylate, 37.5% of ethyl acrylate and 10% of PDMS methacrylate.

The dispersion is stable after storage for 7 days at room temperature (25° C.).

The film obtained with the oily dispersion has the following properties:

| Gloss at 20° | Resistance to fatty substances | Tackiness |
|---|---|---|
| 54 | Resistant to fatty substances | Tackiness |

Study of the Compatibility with Silicone Oils:

The compatibility of the polymer particle dispersions prepared was evaluated by adding to the dispersion 5 different silicone oils (silicone 1 to 5) and by observing whether or not the mixture obtained is stable (homogeneous or heterogeneous mixture).

Silicone 1: Polyphenyltrimethylsiloxydimethylsiloxane (Belsil® PDM 1000 from Wacker) (INCI name: Trimethylsiloxyphenyl dimethicone)
Silicone 2: cyclohexadimethylsiloxane
Silicone 3: 3-octylheptamethyltrisiloxane (Dow Corning FZ-3196 from Dow Corning)
Silicone 4: polydimethylsiloxane 5 cSt (Xiameter PMX-200 Silicone Fluid 5CS from Dow Corning)
Silicone 5: dodecamethylpentasiloxane The following results were obtained:

| Example | HC/Si Ratio | S1 | S2 | S3 | S4 | S5 |
|---|---|---|---|---|---|---|
| 1 | 75/25 | + | + | + | + | + |
|   | 50/50 | + | + | + | − | + |
|   | 25/75 | − | + | + | − | − |
| 2 | 75/25 | + | − | + | − | − |
|   | 50/50 | + | − | + | − | − |
|   | 25/75 | − | − | + | − | − |
| 3 | 75/25 | + | + | + | + | + |
|   | 50/50 | + | + | + | − | + |
|   | 25/75 | + | − | + | − | − |
| 4 | 75/25 | + | + | + | + | + |
|   | 50/50 | + | + | + | − | + |
|   | 25/75 | − | + | + | − | − |
| 5 | 75/25 | + | + | + | + | + |
|   | 50/50 | + | + | + | + | + |
|   | 25/75 | + | + | + | + | + |
| 6 | 75/25 | + | + | + | + | + |
|   | 50/50 | + | + | + | + | + |
|   | 25/75 | + | + | + | + | + |
| 7 | 75/25 | + | + | + | + | + |
|   | 50/50 | + | + | + | + | + |
|   | 25/75 | + | + | + | + | + |

HC/Si ratio: weight ratio of hydrocarbon-based oil (isododecane)/silicone oil present in the polymer particle dispersion.

The results obtained show that the dispersions of examples 5 to 7 have good compatibility with the five silicone oils in the three oil ratios. The dispersions of examples 1, 3 and 4 have good compatibility with the five silicone oils in the HC/Si ratio=75/25 and with four silicone oils in the 50/50 ratio and with two silicone oils in the 25/75 ratio. The dispersion of example 2 is entirely compatible with silicone 3 (all ratios) and with silicone 1 (25/75 and 50/50 ratios).

EXAMPLES 8 AND 9

Two oily dispersions of copolymer of isobornyl acrylate, methyl acrylate and a polydimethylsiloxane methacrylate in which the PDMS chain has a different molecular weight were prepared according to the procedure of example 1.

All the dispersions comprise in total (stabilizer+particles) 20% of isobornyl acrylate, 78% of methyl acrylate and 2% of PDMS methacrylate.

The compatibility of these two dispersions with the five silicone oils was evaluated.

EXAMPLE 8

Step 1: 50 g of isobornyl acrylate, 5 g of methyl acrylate, 4 g of polydimethylsiloxane methacrylate (X-22-2475 from Shin-Etsu, containing a PDMS chain with a molecular weight of 420 g/mol), 0.59 g of Trigonox 21, 120 g of isododecane; followed by addition, after reaction, of 68 g of isododecane Step 2: 191 g of methyl acrylate, 1.91 g of Trigonox 21S, 191 g of isododecane. After reaction, addition of 300 g of isododecane and evaporation to obtain a solids content of 44% by weight.

A dispersion in isododecane of polymethyl acrylate particles stabilized with a polyisobornyl acrylate/methyl acrylate/PDMS acrylate (84.7/8.5/6.8) stabilizer was obtained.

The oily dispersion contains in total (stabilizer+particles) 20% of isobornyl acrylate, 78% of methyl acrylate and 2% of PDMS methacrylate.

The dispersion is stable after storage for 7 days at room temperature (25° C.). The film obtained is non-tacky.

EXAMPLE 9

Step 1: 50 g of isobornyl acrylate, 5 g of methyl acrylate, 4 g of polydimethylsiloxane methacrylate (X-22-2426 from Shin-Etsu, containing a PDMS chain of 12 000 g/mol), 0.59 g of Trigonox 21, 120 g of isododecane; followed by addition, after reaction, of 68 g of isododecane Step 2: 191 g of methyl acrylate, 1.91 g of Trigonox 21S, 191 g of isododecane. After reaction, addition of 300 g of isododecane and evaporation to obtain a solids content of 47% by weight.

A dispersion in isododecane of polymethyl acrylate particles stabilized with a polyisobornyl acrylate/methyl acrylate/PDMS acrylate (84.7/8.5/6.8) stabilizer was obtained.

The dispersion is stable after storage for 7 days at room temperature (25° C.). The film obtained is non-tacky.

The following compatibility results were obtained:

| Example | HC/Si Ratio | S1 | S2 | S3 | S4 | S5 |
|---|---|---|---|---|---|---|
| 8 | 75/25 | + | + | + | − | + |
|   | 50/50 | + | − | − | − | − |
|   | 25/75 | − | − | − | − | − |
| 9 | 75/25 | + | + | + | − | + |
|   | 50/50 | + | + | + | − | + |
|   | 25/75 | − | + | − | − | − |

The results obtained show that the dispersion of example 9 has greater compatibility with the silicone oils than that of example 8. The latter dispersion is compatible with four silicone oils at the 75/25 ratio.

Study of the Ratio of Silicone Macromonomer in the Stabilizer:

EXAMPLES 1, 10, 11 (INVENTION) AND 12 TO 14 (OUTSIDE THE INVENTION)

Five oily dispersions of copolymer of isobornyl acrylate, methyl acrylate, ethyl acrylate and polydimethylsiloxane methacrylate (X-22-2426 from Shin-Etsu, with a PDMS chain of 12 000 g/mol) were prepared, according to the procedure of example 1, by varying the content of silicone macromonomer (content compensated on those of the methyl and ethyl acrylates).

EXAMPLE 10

Step 1: 50 g of isobornyl acrylate, 2 g of methyl acrylate, 2 g of ethyl acrylate, 5 g of polydimethylsiloxane methacrylate (X-22-2426 from Shin-Etsu), 0.59 g of Trigonox 21, 120 g of isododecane; followed by addition, after reaction, of 68 g of isododecane.

Step 2: 95.5 g of methyl acrylate, 95.5 g of ethyl acrylate, 1.91 g of Trigonox 21S, 191 g of isododecane. After reaction, addition of 300 g of isododecane and evaporation to obtain a solids content of 43% by weight.

A dispersion in isododecane of polymethyl acrylate/ethyl acrylate particles (50/50) stabilized with a polyisobornyl acrylate/methyl acrylate/ethyl acrylate/PDMS acrylate (84.7/3.4/3.4/8.5) stabilizer was obtained.

The oily dispersion contains in total (stabilizer+particles) 20% of isobornyl acrylate, 39% of methyl acrylate, 39% of ethyl acrylate and 2% of PDMS methacrylate.

EXAMPLE 11

Step 1: 50 g of isobornyl acrylate, 2 g of methyl acrylate, 2 g of ethyl acrylate, 10 g of polydimethylsiloxane methacrylate (X-22-2426 from Shin-Etsu), 0.64 g of Trigonox 21, 120 g of isododecane; followed by addition, after reaction, of 78 g of isododecane.

Step 2: 93 g of methyl acrylate, 93 g of ethyl acrylate, 1.86 g of Trigonox 21S, 186 g of isododecane. After reaction, addition of 300 g of isododecane and evaporation to obtain a solids content of 46% by weight.

A dispersion in isododecane of polymethyl acrylate/ethyl acrylate particles (50/50) stabilized with a polyisobornyl acrylate/methyl acrylate/ethyl acrylate/PDMS acrylate (78.2/3.1/3.1/15.6) stabilizer was obtained.

EXAMPLE 12

Step 1: 50 g of isobornyl acrylate, 2 g of methyl acrylate, 2 g of ethyl acrylate, 15.2 g of polydimethylsiloxane methacrylate (X-22-2426 from Shin-Etsu), 0.7 g of Trigonox 21, 120 g of isododecane; followed by addition, after reaction, of 78 g of isododecane.

Step 2: 90 g of methyl acrylate, 90 g of ethyl acrylate, 1.8 g of Trigonox 21S, 180 g of isododecane. After reaction, addition of 300 g of isododecane and evaporation.

An unstable dispersion in isododecane of polymethyl acrylate/ethyl acrylate particles (50/50) in the presence of a polyisobornyl acrylate/methyl acrylate/ethyl acrylate/PDMS acrylate (72.5/2.9/2.9/21.7) stabilizer was obtained.

The unstable oily dispersion contains in total (stabilizer+particles) 20% of isobornyl acrylate, 37% of methyl acrylate, 37% of ethyl acrylate and 6% of PDMS methacrylate.

EXAMPLE 13

Step 1: 50 g of isobornyl acrylate, 2 g of methyl acrylate, 2 g of ethyl acrylate, 25.10 g of polydimethylsiloxane methacrylate (X-22-2426 from Shin-Etsu), 0.79 g of Trigonox 21, 120 g of isododecane; followed by addition, after reaction, of 78 g of isododecane.

Step 2: 85.5 g of methyl acrylate, 85.5 g of ethyl acrylate, 1.71 g of Trigonox 21S, 171 g of isododecane. After reaction, addition of 300 g of isododecane and evaporation.

An unstable dispersion in isododecane of polymethyl acrylate/ethyl acrylate particles (50/50) in the presence of a polyisobornyl acrylate/methyl acrylate/ethyl acrylate/PDMS acrylate (78.2/3.1/3.1/15.6) stabilizer was obtained.

The unstable oily dispersion contains in total (stabilizer+particles) 20% of isobornyl acrylate, 35% of methyl acrylate, 35% of ethyl acrylate and 10% of PDMS methacrylate.

EXAMPLE 14

Step 1: 50 g of isobornyl acrylate, 2 g of methyl acrylate, 2 g of ethyl acrylate, 20 g of polydimethylsiloxane methacrylate (X-22-2426 from Shin-Etsu), 0.74 g of Trigonox 21, 120 g of isododecane; followed by addition, after reaction, of 78 g of isododecane.

Step 2: 88 g of methyl acrylate, 88 g of ethyl acrylate, 1.76 g of Trigonox 21S, 176 g of isododecane. After reaction, addition of 300 g of isododecane and evaporation.

An unstable dispersion in isododecane of polymethyl acrylate/ethyl acrylate particles (50/50) in the presence of a polyisobornyl acrylate/methyl acrylate/ethyl acrylate/PDMS acrylate (78.2/3.1/3.1/15.6) stabilizer was obtained.

The unstable oily dispersion contains in total (stabilizer+particles) 20% of isobornyl acrylate, 36% of methyl acrylate, 36% of ethyl acrylate and 8% of PDMS methacrylate.

The stability of each dispersion after 12 hours of storage at room temperature was evaluated. The following results were obtained:

| Examples | Monomers | Mass percentage of the monomers | Solvent | Solids content (%) | Stability |
|---|---|---|---|---|---|
| 10 | IA | 20 | Isododecane | 43.44 | Yes |
|  | MA | 39 |  |  |  |
|  | EA | 39 |  |  |  |
|  | PDMSM12K | 2 |  |  |  |
| 11 | IA | 20 | Isododecane | 45.80 | Yes |
|  | MA | 38 |  |  |  |
|  | EA | 38 |  |  |  |
|  | PDMSM 12K | 4 |  |  |  |
| 1 | IA | 20 | Isododecane | 42.6 | Yes |
|  | MA | 37.5 |  |  |  |
|  | EA | 37.5 |  |  |  |
|  | PDMSM 12K | 5 |  |  |  |
| 12 | IA | 20 | Isododecane | — | No |
|  | MA | 37 |  |  |  |
|  | EA | 37 |  |  |  |
|  | PDMSM12K | 6 |  |  |  |
| 13 | IA | 20 | Isododecane | — | No |
|  | MA | 35 |  |  |  |
|  | EA | 35 |  |  |  |
|  | PDMSM 12K | 10 |  |  |  |
| 14 | IA | 20 | Isododecane | — | No |
|  | MA | 36 |  |  |  |
|  | EA | 36 |  |  |  |
|  | PDMSM12K | 8 |  |  |  |

IA = Isobornyl Acrylate -
MA = Methyl Acrylate -
EA = Ethyl Acrylate -
PDMSM12k = PDMS Methacrylate (X-22-2426 from Shin-Etsu)

The results obtained show that when PDMS methacrylate is present in an amount of greater than or equal to 6% of the total weight of the monomers forming the stabilizer, the dispersions (examples 12 to 14) are unstable. The dispersions of examples 1, 10 and 11 according to the invention are stable.

Study of the Ratio of Silicone Macromonomer in the Polymer of the Particles:

EXAMPLE 2 (INVENTION) AND 15 (OUTSIDE THE INVENTION)

A dispersion of copolymer of isobornyl acrylate, methyl acrylate, ethyl acrylate and polydimethylsiloxane methacrylate (X-22-2426 from Shin-Etsu, with a PDMS chain of 12 000 g/mol) was prepared, according to the procedure of example 2, by varying the content of silicone macromonomer (content compensated on those of the methyl and ethyl acrylates).

EXAMPLE 15

Step 1: 50 g of isobornyl acrylate, 2 g of methyl acrylate, 2 g of ethyl acrylate, 0.54 g of Trigonox 21S, 120 g of isododecane; followed by addition, after reaction, of 78 g of isododecane.
Step 2: 98 g of methyl acrylate, 73 g of ethyl acrylate, 25 g of polydimethylsiloxane methacrylate (X-22-2426 from Shin-Etsu), 1.96 g of Trigonox 21S, 196 g of isododecane. After reaction, addition of 0.3 liter of isododecane and evaporation.
An unstable dispersion in isododecane of polymethyl acrylate/ethyl acrylate particles (50/50) in the presence of a polyisobornyl acrylate/methyl acrylate/ethyl acrylate/PDMS acrylate (67.6/2.7/2.7/20) stabilizer was obtained.

The unstable oily dispersion contains in total (stabilizer+particles) 20% of isobornyl acrylate, 40% of methyl acrylate, 20% of ethyl acrylate and 20% of PDMS methacrylate.

The stability of each dispersion after 12 hours of storage at room temperature was evaluated. The following results were obtained:

| Examples | Monomers | Mass percentage of the monomers | Solvent | Solids content (%) | Stability |
|---|---|---|---|---|---|
| 2 | IA | 20 | Isododecane | 39.82 | Yes |
|  | MA | 40 |  |  |  |
|  | EA | 30 |  |  |  |
|  | PDMSM12K | 10 |  |  |  |
| 15 | IA | 20 | Isododecane | — | No |
|  | MA | 40 |  |  |  |
|  | EA | 20 |  |  |  |
|  | PDMSM 12K | 20 |  |  |  |

IA = Isobornyl Acrylate -
MA = Methyl Acrylate -
EA = Ethyl Acrylate -
PDMSM12k = PDMS Methacrylate (X-22-2426 from Shin-Etsu)

The results obtained show that when the silicone macromonomer is present in the polymer of the particles in a content of 20%, the dispersion is unstable.

Study of the Ratio of Silicone Macromonomer in the Stabilizer and in the Polymer of the Particles:

EXAMPLES 3, 16, 17 (INVENTION) AND 18 (OUTSIDE THE INVENTION)

Three dispersions of copolymer of isobornyl acrylate, methyl acrylate, ethyl acrylate and polydimethylsiloxane methacrylate (X-22-2426 from Shin-Etsu, with a PDMS chain of 12 000 g/mol) were prepared, according to the procedure of example 3, by varying the content of silicone macromonomer (content compensated on those of the methyl and ethyl acrylates) in the stabilizer and in the polymer of the particles.

EXAMPLE 16

Step 1: 50 g of isobornyl acrylate, 2 g of methyl acrylate, 2 g of ethyl acrylate, 12.5 g of polydimethylsiloxane methacrylate (X-22-2426 from Shin-Etsu), 0.665 g of Trigonox 21S, 120 g of isododecane; followed by addition, after reaction, of 78 g of isododecane.
Step 2: 91.5 g of methyl acrylate, 66.5 g of ethyl acrylate, 25 g of polydimethylsiloxane methacrylate (X-22-2426 from Shin-Etsu), 1.83 g of Trigonox 21S, 183 g of isododecane. After reaction, addition of 300 g of isododecane and evaporation to obtain a solids content of 44% by weight.
A dispersion in isododecane of methyl acrylate/ethyl acrylate/PDMS acrylate (50/36.3/13.7) copolymer particles stabilized with an isobornyl acrylate/methyl acrylate/ethyl acrylate/PDMS methacrylate (75.2/3/3/18.8) statistical copolymer was obtained.

The oily dispersion contains in total (stabilizer+particles) 20% of isobornyl acrylate, 37.5% of methyl acrylate, 27.5% of ethyl acrylate and 25% of PDMS methacrylate.

EXAMPLE 17

Step 1: 50 g of isobornyl acrylate, 2 g of methyl acrylate, 2 g of ethyl acrylate, 12.5 g of polydimethylsiloxane methacrylate (X-22-2426 from Shin-Etsu), 0.665 g of Trigonox 21S, 120 g of isododecane; followed by addition, after reaction, of 78 g of isododecane.

Step 2: 91.5 g of methyl acrylate, 41.5 g of ethyl acrylate, 50 g of polydimethylsiloxane methacrylate (X-22-2426 from Shin-Etsu), 1.83 g of Trigonox 21S, 183 g of isododecane. After reaction, addition of 300 g of isododecane and evaporation to obtain a solids content of 42% by weight.

A dispersion in isododecane of methyl acrylate/ethyl acrylate/PDMS acrylate (50/22.7/27.3) copolymer particles stabilized with an isobornyl acrylate/methyl acrylate/ethyl acrylate/PDMS methacrylate (75.2/3/3/18.8) statistical copolymer was obtained.

The oily dispersion contains in total (stabilizer+particles) 20% of isobornyl acrylate, 37.5% of methyl acrylate, 17.5% of ethyl acrylate and 25% of PDMS methacrylate.

EXAMPLE 18

Step 1: 50 g of isobornyl acrylate, 2 g of methyl acrylate, 2 g of ethyl acrylate, 25 g of polydimethylsiloxane methacrylate (X-22-2426 from Shin-Etsu), 0.79 g of Trigonox 21S, 120 g of isododecane; followed by addition, after reaction, of 78 g of isododecane.

Step 2: 85.2 g of methyl acrylate, 60.2 g of ethyl acrylate, 25 g of polydimethylsiloxane methacrylate (X-22-2426 from Shin-Etsu), 1.70 g of Trigonox 21S, 170 g of isododecane. After reaction, addition of 300 g of isododecane and evaporation.

An unstable dispersion in isododecane of methyl acrylate/ethyl acrylate/PDMS acrylate (50/35.3/14.7) copolymer particles in the presence of an isobornyl acrylate/methyl acrylate/ethyl acrylate/PDMS methacrylate (63.3/2.5/2.5/31.7) statistical copolymer was obtained.

The oily dispersion contains in total (stabilizer+particles) 20% of isobornyl acrylate, 35% of methyl acrylate, 25% of ethyl acrylate and 20% of PDMS methacrylate.

The stability of each dispersion after 12 hours of storage at room temperature was evaluated. The following results were obtained:

| Examples | Monomers | Mass percentage of the monomers | Solvent | Solids content (%) | Stability |
|---|---|---|---|---|---|
| 3 | IA | 20 | Isododecane | 45.02 | Yes |
|  | MA | 37.5 |  |  |  |
|  | EA | 32.5 |  |  |  |
|  | PDMSM12K (stabilizer) | 5 |  |  |  |
|  | PDMSM12K (particles) | 5 |  |  |  |
| 16 | IA | 20 | Isododecane | 44.10 | Yes |
|  | MA | 37.5 |  |  |  |
|  | EA | 27.5 |  |  |  |
|  | PDMSM12K (stabilizer) | 5 |  |  |  |
|  | PDMSM12K (particles) | 10 |  |  |  |
| 17 | IA | 20 | Isododecane | 38.94 | Yes |
|  | MA | 37.5 |  |  |  |
|  | EA | 17.5 |  |  |  |
|  | PDMSM12K (stabilizer) | 5 |  |  |  |
|  | PDMSM12K (particles) | 20 |  |  |  |
| 18 | IA | 20 | Isododecane | — | No |
|  | MA | 35 |  |  |  |
|  | EA | 25 |  |  |  |
|  | PDMSM12K (stabilizer) | 10 |  |  |  |
|  | PDMSM12K (particles) | 10 |  |  |  |

IA = Isobornyl Acrylate -
MA = Methyl Acrylate -
EA = Ethyl Acrylate -
PDMSM12k = PDMS Methacrylate (X-22-2426 from Shin-Etsu)

The results obtained show that the dispersions (examples 3, 16, 17) containing 5% of silicone macromonomer in the stabilizer and from 5% to 20% of silicone macromonomer in the particles are stable, whereas the dispersion of example 18 containing 10% of silicone macromonomer in the stabilizer and 10% of silicone macromonomer in the particles is unstable.

Study of Compatibility with the Propellant Isobutane:

The following compositions were prepared with the oily dispersions of examples 1, 3 and 4:

| Oily dispersion | 8% AM |
| PDMS 10 cSt oil | 29% |
| Isododecane | 63% |

4.45 g of each composition were introduced into a glass aerosol bottle, a dispensing valve was then crimped onto the bottle, and 25.25 g of isobutane were then introduced into the can.

The appearance (stability) of the composition thus packaged was observed. The following results were obtained:

| | Oily dispersion example | | |
|---|---|---|---|
| | 1 | 3 | 4 |
| Stability | Stable | Stable | Stable |

The results obtained show that the oily dispersions of examples 1, 3 and 4 are compatible with isobutane, in the presence of PDMS oil. They are thus suitable for the formulation of aerosol compositions.

EXAMPLE 19

A skin makeup composition comprising the ingredients below is prepared:

| Polymer dispersion of Example 1 | 85% |
| Dodecamethylpentasiloxane | 10% |
| Iron oxides | 5% |

The composition applied to the skin makes it possible to obtain a glossy makeup film that is resistant to oils and non-tacky.

The polymer dispersion of Example 1 may be replaced with the dispersions of Examples 2 to 7.

EXAMPLE 20

A lip makeup composition comprising the ingredients below is prepared:

| | |
|---|---|
| Polymer dispersion of Example 1 | 84% |
| Polyphenyltrimethylsiloxydimethylsiloxane (Belsil ® PDM 1000 from Wacker) | 15% |
| Red 7 | 1% |

The composition applied to the lips makes it possible to obtain a glossy makeup film that is resistant to oils and non-tacky.

The polymer dispersion of Example 1 may be replaced with the dispersions of Examples 2 to 7.

EXAMPLE 21

An eyelash makeup composition comprising the ingredients below is prepared:

| | |
|---|---|
| Polymer dispersion of Example 1 | 60% |
| Isododecane | 20% |
| Black iron oxides | 20% |

The composition applied to the eyelashes makes it possible to obtain a glossy makeup film that is resistant to oils and non-tacky.

The polymer dispersion of Example 1 may be replaced with the dispersions of Examples 2 to 7.

EXAMPLE 22

A film-forming aerosol composition for the skin comprising the following ingredients is prepared (packaged in an aerosol can equipped with a dispensing valve):

| | |
|---|---|
| Polymer dispersion of Example 1 | 1.2% AM |
| PDMS 10 cSt | 4.35% |
| Isododecane | 9.45% |
| Isobutane | qs 100% |

The composition is vaporized onto the skin and forms a film after drying.

The invention claimed is:

1. A dispersion of particles of at least one polymer stabilized with a stabilizer in a nonaqueous medium containing at least one hydrocarbon-based oil, the polymer of the particles being a polymer of $C_1$-$C_4$ alkyl (meth)acrylate and optionally of a silicone macromonomer (I):

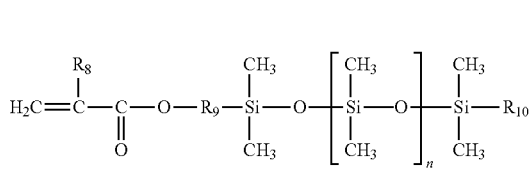

(I)

in which:
R8 denotes a hydrogen atom or a methyl group;
R9 denotes a linear or branched divalent hydrocarbon-based group containing from 1 to 10 carbon atoms and optionally containing one or two —O— ether bonds;
R10 denotes a linear or branched alkyl group containing from 1 to 10 carbon atoms;
n denotes an integer ranging from 1 to 300; wherein the polymer of the particles is present in a content ranging from 20% to 60% by weight, relative to the total weight of the dispersion;
the stabilizer being a statistical polymer comprising from 50% to 100% by weight, relative to the total weight of the stabilizer, of isobornyl acrylate, from 0 to 50% by weight of $C_1$-$C_4$ alkyl (meth)acrylate and optionally silicone macromonomer (I):
wherein the weight of stabilizer relative to the total weight of the monomers used in the stabilizer and polymer of the particles is 10% to 30% by weight;
the stabilizer and/or the polymer of the particles comprising at least the silicone macromonomer (I), and:
(i) when the stabilizer comprises the silicone macromonomer (I), the macromonomer is present in the stabilizer in a content of less than or equal to 5.5% by weight, relative to the total weight of the combination of the stabilizer plus the polymer of the particles; the polymer of the particles optionally comprising said silicone macromonomer (I) in a content of less than or equal to 28% by weight, relative to the total weight of the combination of the stabilizer plus the polymer of the particles;
(ii) when the polymer of the particles comprises the silicone macromonomer (I) and the stabilizer does not comprise silicone macromonomer (I), the macromonomer is present in a content of less than or equal to 18% by weight, relative to the total weight of the combination of the stabilizer plus the polymer of the particles.

2. The dispersion as claimed in claim 1, wherein the polymer of the particles is a methyl acrylate and/or ethyl acrylate polymer.

3. The dispersion as claimed in claim 1, wherein the polymer of the particles comprises an ethylenically unsaturated acid monomer or the anhydride thereof.

4. The dispersion as claimed in claim 1, wherein the polymer of the particles comprises from 62% to 100% by weight of $C_1$-$C_4$ alkyl (meth)acrylate, from 0 to 38% by weight of the silicone macromonomer (I) and from 0 to 20% by weight of ethylenically unsaturated acid monomer, relative to the total weight of the polymer.

5. The dispersion as claimed in claim 1, wherein the polymer of the particles is chosen from:
methyl acrylate homopolymers
methyl acrylate/silicone macromonomer (I) copolymers
ethyl acrylate homopolymers
ethyl acrylate/silicone macromonomer (I) copolymers
methyl acrylate/ethyl acrylate copolymers
methyl acrylate/ethyl acrylate/silicone macromonomer (I) copolymers
methyl acrylate/ethyl acrylate/acrylic acid copolymers
methyl acrylate/ethyl acrylate/acrylic acid/silicone macromonomer (I) copolymers
methyl acrylate/ethyl acrylate/maleic anhydride copolymers
methyl acrylate/ethyl acrylate/maleic anhydride/silicone macromonomer (I) copolymers
methyl acrylate/acrylic acid copolymers
methyl acrylate/acrylic acid/silicone macromonomer (I) copolymers
ethyl acrylate/acrylic acid copolymers
ethyl acrylate/acrylic acid/silicone macromonomer (I) copolymers
methyl acrylate/maleic anhydride copolymers methyl acrylate/maleic anhydride/silicone macromonomer (I) copolymers ethyl acrylate/maleic anhydride/silicone macromonomer (I) copolymers and ethyl acrylate/maleic anhydride copolymers.

6. The dispersion as claimed in claim 1, wherein the polymer particles have an average size ranging from 50 to 500 nm.

7. The dispersion as claimed in claim 1, wherein the stabilizer is a polymer comprising from 50% to 100% by weight of isobornyl acrylate, from 0 to 50% by weigh of $C_1$-$C_4$ alkyl (meth)acrylate and optionally the silicone macromonomer (I).

8. The dispersion as claimed in claim 1, wherein the stabilizer is chosen from:

isobornyl acrylate homopolymers isobornyl acrylate/methyl acrylate copolymers isobornyl acrylate/methyl acrylate/ethyl acrylate copolymers isobornyl acrylate/methyl acrylate/ethyl acrylate/silicone macromonomer (I) copolymers.

9. The dispersion as claimed in claim 1, wherein the silicone macromonomer (I) is present in the stabilizer in a content of less than or equal to 5.5% by weight relative to the total weight of the combination of the stabilizer plus the polymer of the particles; and the silicone macromonomer (I) is not present in the polymer of the particles.

10. The dispersion as claimed in claim 9, wherein the combination of the stabilizer plus the polymer of the particles present in the dispersion comprises from 5% to 50% by weight of polymerized isobornyl acrylate, from 44.5% to 89.5% by weight of polymerized $C_1$-$C_4$ alkyl (meth)acrylate and from 0.1% to 5.5% by weight of silicone macromonomer (I), relative to the total weight of the combination of the stabilizer plus the polymer of the particles.

11. The dispersion as claimed in claim 1, wherein the silicone macromonomer (I) is present in the stabilizer in a content of less than or equal to 5.5% by weight relative to the total weight of the combination of the stabilizer plus the polymer of the particles; and it is present in the polymer of the particles in a content of less than or equal to 28% by weight relative to the total weight of the combination of the stabilizer plus the polymer of the particles.

12. The dispersion as claimed in claim 11, wherein the combination of the stabilizer plus the polymer of the particles present in the dispersion comprises from 5% to 50% by weight of polymerized isobornyl acrylate, from 16.5% to 94.9% by weight of polymerized $C_1$-$C_4$ alkyl (meth)acrylate and from 0.1% to 33.5% by weight of silicone macromonomer (I), relative to the total weight of the combination the stabilizer plus the polymer of the particles.

13. The dispersion as claimed claim 1, wherein the silicone macromonomer (I) is present in the polymer of the particles in a content of less than or equal to 18% by weight relative to the total weight of the combination of the stabilizer plus the polymer of the particles; and it is not present in the stabilizer.

14. The dispersion as claimed in claim 13, wherein the combination of the stabilizer plus the polymer of the particles present in the dispersion comprises from 5% to 50% by weight of polymerized isobornyl acrylate, from 32% to 94.9% by weight of polymerized $C_1$-$C_4$ alkyl (meth)acrylate and from 0.1% to 18% by weight of silicone macromonomer (I), relative to the total weight of the combination of the stabilizer plus the polymer of the particles.

15. The dispersion as claimed in claim 1, wherein the hydrocarbon-based oil is chosen from hydrocarbon-based oils containing from 8 to 16 carbon atoms.

16. The dispersion according to claim 1, wherein the hydrocarbon-based oil is isododecane.

17. A composition comprising, in a physiologically acceptable medium, a polymer dispersion as claimed in claim 1.

18. The composition as claimed in claim 17, wherein it comprises a cosmetic additive chosen from water, fragrances, preserving agents, fillers, dyestuffs, UV-screening agents, oils, waxes, surfactants, moisturizers, vitamins, ceramides, antioxidants, free-radical scavengers, polymers and thickeners.

19. The composition as claimed in claim 17, which comprises a silicone oil.

20. The composition as claimed in claim 19, wherein the silicone oil is present in a content ranging from 0.1% to 60% by weight, relative to the total weight of the composition.

21. The composition as claimed claim 17, which is an aerosol composition containing a propellant.

22. A nontherapeutic cosmetic process for treating keratin materials, comprising the application to the keratin materials of a composition as claimed in claim 17.

\* \* \* \* \*